United States Patent [19]

McGredy, IV

[11] Patent Number: Plant 7,472

[45] Date of Patent: Mar. 19, 1991

[54] SHRUB ROSE PLANT NAMED 'MACFIRWAL'

[75] Inventor: Sam McGredy, IV, Castor Bay, New Zealand

[73] Assignee: Roses by Fred Edmunds, Wilsonville, Oreg.

[21] Appl. No.: 468,273

[22] Filed: Jan. 17, 1990

[51] Int. Cl.[5] ..... A01H 5/00

[52] U.S. Cl. ..... Plt./1

[58] Field of Search ..... Plt. 1

*Primary Examiner*—James R. Feyrer

*Attorney, Agent, or Firm*—Christie, Parker & Hale

[57] ABSTRACT

A new and unusual, red and yellow bicolor shrub rose.

1 Drawing Sheet

SUMMARY OF THE INVENTION

The present invention relates to a new and distinct variety of rose plant of the shrub rose class, which was originated by my crossing as seed parent the variety known as "Sexy Rexy" and as pollen parent the variety known as "Maestro". The varietal denomination of this new rose is "Macfirwal".

Among the novel characteristics possessed by this new variety which distinguish it from its parents and all other varieties of which I am aware are its unusual red and yellow bicolored flowers in this class of rose. Flowers open well and retain bicolor effect as bloms age. Asexual reproduction by propagation by cuttings of the new variety as performed in Clackamas Country, Oregon, shows that the foregoing and other distinghishing characteristics come true to form and are established and transmitted through succeeding propagations.

BRIEF DESCRIPTION OF DRAWING

The accompanying drawing shows typical specimens of the vegetative growth and flowers of the new variety in different stages of development and depicted in color as nearly true as it is reasonably possible to make the same in a color illustration of this character.

DESCRIPTION OF PREFERRED EMBODIMENT

The following is a detailed description of my new variety, with color terminology in accordance with The Royal Horticultural Society Color Chart (R.H.S.C.C.). The terminology used in color description herein refers to plate numbers in the aforementioned color chart, e.g., "44B" is plate 44B of The Royal Horticultural Society Color Chart.

Parentage: Seedling.

*Seed parent.*—"Sexy Rexy".

*Pollen parent.*—"Maestro".

Class: Shrub.

The following observations are made of specimens grown outdoors in Clackamas County, Or., during the month of October.

FLOWER

Blooming habit: Continuous.

A. Bud:

(1) *Size.*—Small, about 3-cm.

(2) *Form.*—Flared, exhibition.

(3) *Color.*—As sepals divide, bud color is near 44B flushed with yellow and with a yellow base near petal attachment, as shown in the illustration in the area not affected by excessive lighting.

(4) *Sepals.*—Longer than bud, simple, glabrous outside, finely hirsute inside.

(5) *Penduncle.*—Length — about 5 to 6 cm. Aspect — straight, upright with scattered tiny prickles. Strength — erect. Color — near 138B.

B. Bloom:

(1) *Size.*—Average size when fully expanded — about 8 to 10 cm.

(2) *Borne.*—Sprays of 5 to 25 blooms.

(3) *Form.*—Urn shaped in bud, opens quickly, becoming flat. Margins undulate.

(4) *Petalage.*—Number of petals under normal conditions — under 18, semi-double.

(5) *Color.*—After sepals fall and before petals separate bud coloring is near 44B flushed with yellow and with a yellow base. After petals unfurl, which occurs rapidly, coloring before aging is a cobmination different red tones on the outer portion of petal top surface and yellow tones at the inner portions of the petal top surface toward the flower center. The color range of the red tones viewing the bloom from the top surface is from near 46B of the deepest red tone to lighter shades, near 44D to C. Also visible are some intermediate orange red tones, near 42C to near 44B. The coloring of the flower center ranges from near 21A to D, beginning at a relatively abrupt color demarcation. The red coloring of the petal top surface may be imbued with light toned highlights and some petal margins show light edges, more pronounced as blooms age.

The petal undersurface is mainly light pink, near 36 A to D, but with a yellow cast. The lower segments of the petals are near 21 C to D with the yellow coloring appearing deeper toned, near 21 A to B, in bud form and in newly opened blooms. Unlike the petal top surface, the yellow and pink/red coloring wash into one another rather than being separated by an abrupt demarcation.

As the blooms age, the red tones on the petal top surfae deepen and become more blue-red. Near white or pale yellow intrusion at the margins is evident and the yellow center may lighten somewhat to near white. The petal under surface may darken to include some magenta coloring with near white washing toward the point of petal attachment.

Overall tonality viewed from a distance is very attractive bled of red coloring, near 44B which becomes near 45C upon aging.

C. Petals:

(1) *Texture.*—Thick with excellent substance (2) *Appearance.*—Inside slightly velvety making color seem iridescent, smooth reverse.

(3) *Form.*—Broad, fan shaped, some pointed apices.

(4) *Arrangement.*—Regularly arranged, imbricated.

(5) *Petaloids in center.*—Few to none.

(6) *Persistence.*—Drop off cleanly.

(7) *Fragrance.*—Slightly sweet.

(8) *Lasting quality.*—Long lasting quality on plant but due to large number of blooms per stem, is shortlived after cutting.

REPRODUCTIVE ORGANS

A. Stamens, filaments and anthers:

*Arrangement and color.*—Regularly arranged around styles. Color — filaments near 14B.

B. Pollen:

*Color.*—Near 4A.

C. Styles: Medium length, thin, slightly hirsute, color near 47D.

D. Stigmas:

*Color.*—Near 4A.

E. Hips: Globular, about 1¼ cm, near 145A, few seeds, (near 45A), protrude.

PLANT

A. Form: Upright, slightly spreading

B. Growth: Very vigorous to 2-meters, secondary bloom growth arises continually from upper leaf axils below the primary trees, late summer basals

*Height attained.*—About 2-meters in third year

C. Foliage: Compound mostly 5 leaflets.

(1) *Size.*—Medium, 4 to 6 cm.

(2) *Quantity.*—Very abundant with short internodes.

(3) *Color.*—New foliage: Upper side — near 59B. Under side — near 59D. Old foliage: Upper side — near 136B. Under side — near 138C.

(4) *Shape.*—Oval, acuminate rachis fluted on surface.

(5) *Texture.*—Upper side is glabrous, waxy, veining prominent.

(6) *Edge.*—Serrate.

(7) *Serration.*—Ordinary, simple.

(8) *Leaf stem.*—Color — near 138C, fluted on upper edge with few prickles on back Under side — near 138D.

(9) *Stipules.*—Short to long pointed

(10) *Resistance to disease.*—Blackspot — Excellent. Mildew — Excellent. Rust — Excellent.

D. Wood:

(1) *New wood.*—Color — near 146A. Bark — smooth, waxy.

(2) *Old wood.*—Color — near 139B. Bark — smooth with waxy cast.

E. Thorns:

(1) *Thorns.*—Quantity (main stalk) — few to none. On laterals from stalk — few. Form — long, narrow, thin, slightly curved downward. Length — short. Color — near 49A. Position — irregular.

(2) Prickles.—Few to none.

F. Winter hardiness: Survived 14° C. without protection.

I claim:

1. A new and distinct variety of rose plant of the shrub rose class, substantially as shown and described, characterized particularly by attractive red and yellow bicolored flowers borne on a vigorous, resistent plant.

* * * * *

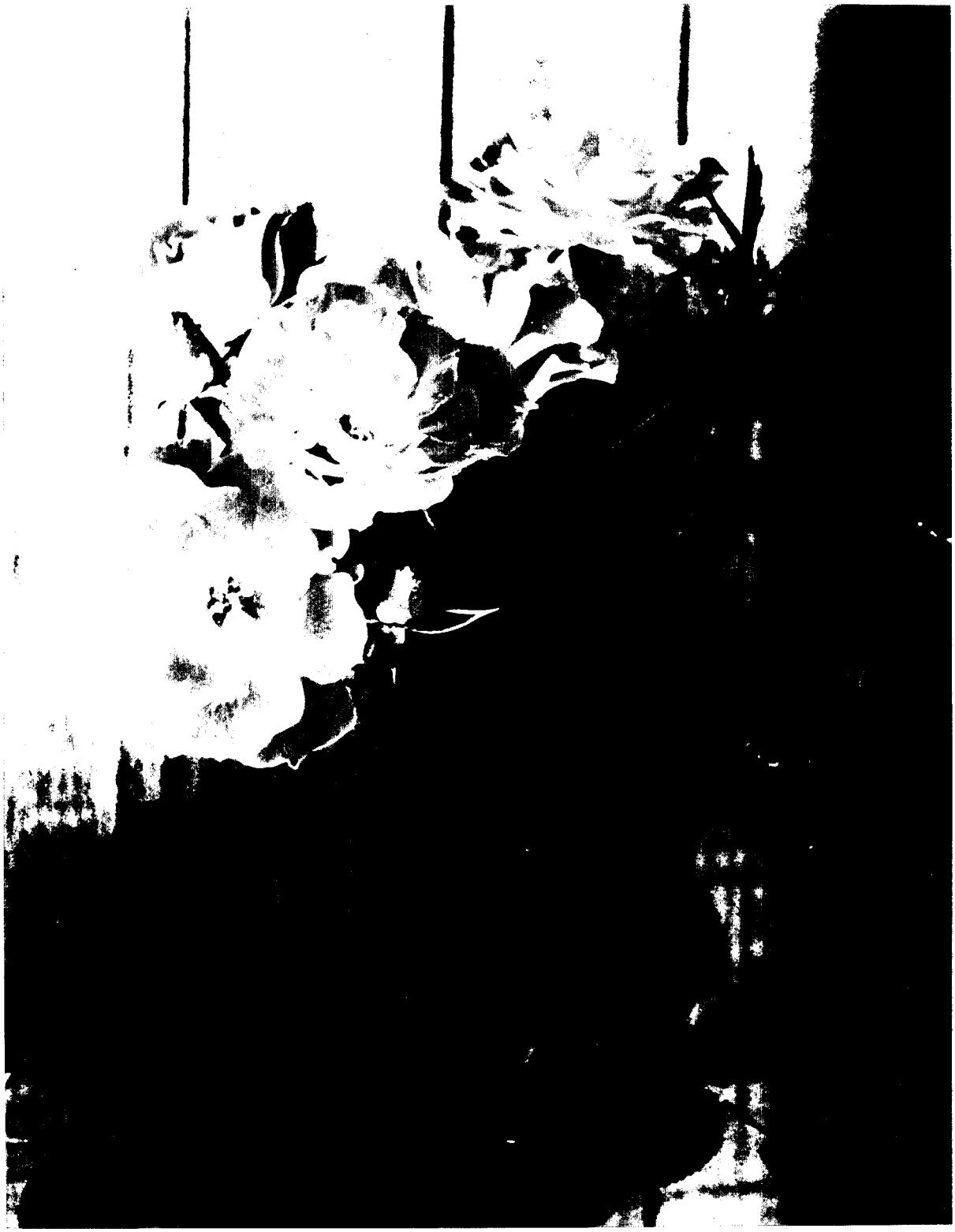

UNITED STATES PATENT AND TRADEMARK OFFICE

CERTIFICATE OF CORRECTION

PATENT NO. : Plant 7,472

DATED : March 19, 1991

INVENTOR(S) : Sam McGredy, IV

It is certified that error appears in the above-identified patent and that said Letters Patent is hereby corrected as shown below:

Title Page:

[75] Inventor, before "New Zealand" insert -- Auckland, --.

Column 1, line 12, change "bloms" to -- blooms --.
Column 1, line 15, change "Country" to -- County --.
Column 1, line 16, change "distinghishing" to -- distinguishing --.
Column 1, line 41, change "Or." to -- Oregon --.

Column 2, line 21, change "cobmination" to -- combination --.
Column 2, line 46, change "surfae" to -- surface --.

Column 3, line 4, change "bled" to -- blend --.

Signed and Sealed this

Fifth Day of January, 1993

*Attest:*

*Attesting Officer*

DOUGLAS B. COMER

*Acting Commissioner of Patents and Trademarks*